(12) United States Patent
Yan et al.

(10) Patent No.: US 8,809,309 B2
(45) Date of Patent: Aug. 19, 2014

(54) USE OF 5α-ANDROSTANE (ALKYL)-3β,5,6β-TRIOL IN PREPARATION OF NEUROPROTECTIVE DRUGS

(75) Inventors: Guangmei Yan, Guangzhou (CN); Haiyan Hu, Guangzhou (CN); Tiandong Leng, Guangzhou (CN); Hanfei Sang, Guangzhou (CN); Jingxia Zhang, Guangzhou (CN); Pengxin Qiu, Guangzhou (CN); Shujia Zhou, Guangzhou (CN); Jiesi Chen, Guangzhou (CN); Xiuhua You, Guangzhou (CN)

(73) Assignee: Guangzhou Cellprotek Pharmaceutical Ltd., Guangzhou, Guangdong (CN)

( * ) Notice: Subject to any disclaimer, the term of this patent is extended or adjusted under 35 U.S.C. 154(b) by 0 days.

(21) Appl. No.: 13/805,436

(22) PCT Filed: Jul. 8, 2011

(86) PCT No.: PCT/CN2011/076967
§ 371 (c)(1),
(2), (4) Date: Dec. 19, 2012

(87) PCT Pub. No.: WO2012/003802
PCT Pub. Date: Dec. 1, 2012

(65) Prior Publication Data
US 2013/0157993 A1     Jun. 20, 2013

(30) Foreign Application Priority Data

Jul. 9, 2010    (CN) .......................... 2010 1 0224173

(51) Int. Cl.
*C07J 1/00* (2006.01)
(52) U.S. Cl.
USPC ....................................................... 514/182
(58) Field of Classification Search
None
See application file for complete search history.

(56) References Cited

U.S. PATENT DOCUMENTS

| | | | | |
|---|---|---|---|---|
| 2003/0060425 A1* | 3/2003 | Ahlem et al. | ................... | 514/26 |
| 2013/0172307 A1 | 7/2013 | Yan et al. | | |

FOREIGN PATENT DOCUMENTS

| | | | |
|---|---|---|---|
| CN | 101961311 B | * | 11/2012 |
| WO | WO 2008155534 | | 12/2008 |

OTHER PUBLICATIONS

Ohuchi et al. The Reaction of Lead Tetraacetate with 3B-Hydroxy Steroids. Chem. Pharm. Bull. (1981) vol. 29 pp. 43-50.*
Brewer G.J. Isolation and culture of adult rat hippocampal neurons, J. Neurosci. Meth, 1997, 71: 143-155.
Celik M. et al. Erythropoietin prevents motor neuron apoptosis and neurologic disability in experimental spinal cord ischemic injury. Proc Natl Acad Sci U S A, 2002, 99: 2258-2263.
International Search Report for PCT/CN2011/076967, issued Oct. 13, 2011.
Johnson S.H. et al. Effects of flunarizine on neurological recovery and spinal cord blood flow in experimental spinal cord ischemia in rabbits. Stroke, 1993, 24: 1547-1553.
Lee M.M. et al. Magnoloi protects cortical neuronal cells from chemical hypoxia in rats, Neuroreport 1998, 9: 3451-3456.
Longa E.Z. et al. Reversible middle cerebral artery occlusion without craniectomy in rats. Stroke 1989, 20(1):84-91.
Sang H. et al. Isoflurane produces delayed preconditioning against spinal cord ischemic injury via release of free radicals in rabbits. Anesthesiology, 2006, 105: 953-960.
Wang Q. et al. Pretreatment with electroacupuncture induces rapid tolerance to focal cerebral ischemia through regulation of endocannabinoid system. Stroke, 2009, 40(6):2157-2164.
Abstract of Uno H, Eisele S, Sakai A, Shelton S, Baker E, DeJesus O, and Holden J. "Neurotoxicity of glucocorticoids in the primate brain." J.Horm Behav., Dec. 1994;28(4):336-48.
Aden P, Goverud I, Liestol K, Løberg EM, Paulsen RE, Maehlen J, and Lømo J. "Low-potency glucocorticoid hydrocortisone has similar neurotoxic effects as high-potency glucocorticoid dexamethasone on neurons in the immature chicken cerebellum." Brain Research, vol. 1236, 2008, pp. 39-48.
Braden BB, Garcia AN, Mennenga SE, Prokai L, Villa SR, Acosta JI, Lefort N, and Simard AR. "Bimonte-Nelson HA., Cognitive-impairing effects of medroxyprogesterone acetate in the rat: independent and interactive effects across time." Psychopharmacology (Berl). Nov. 2011;218(2):405-18.
Caraci F, PistaràV, Corsaro A, Tomasello F, Giuffrida ML, Sortino MA, Nicoletti F, and Copani A. "Neurotoxic properties of the anabolic androgenic steroids nandrolone and methandrostenolone in primary neuronal cultures." J Neurosci Res. Apr. 2011;89(4):592-600.
Cunningham RL, Giuffrida A, Roberts JL. "Androgens induce dopaminergic neurotoxicity via caspase-3-dependent activation of protein kinase Cdelta." Endocrinology Dec. 2009;150(12):5539-48.
Luoma JI, Stern CM, and Mermelstein PG. "Progesterone inhibition of neuronal calcium signaling underlies aspects of progesterone-mediated neuroprotection." J Steroid Biochem Mol Biol 2012;131:30-36.
Nilsen J, Morales A, and Brinton RD. "Medroxyprogesterone acetate exacerbates glutamate excitotoxicity." Gynecol. Endocrinol. Jul. 2006;22(7):355-61.

(Continued)

*Primary Examiner* — Melenie McCormick
*Assistant Examiner* — Taina D Matos Negron
(74) *Attorney, Agent, or Firm* — Finnegan, Henderson, Farabow, Garrett & Dunner LLP

(57) ABSTRACT

Disclosed is the use of 5α-androstane(alkyl)-3β,5,6β-triol in preparing neuroprotective drugs. The compound has significant protective effect against neuron injuries caused by cerebral ischemia, spinal cord ischemia or hypoxia and has no obvious toxic reaction within effective dose thereof.

4 Claims, 4 Drawing Sheets

(56) References Cited

OTHER PUBLICATIONS

Orlando R, Caruso A, Molinaro G, Motolese M, Matrisciano F, Togna G, Melchiorri D, Nicoletti F, and Bruno V. "Nanomolar concentrations of anabolic-androgenic steroids amplify excitotoxic neuronal death in mixed mouse cortical cultures." Brain Res. Aug. 24, 2007;1165:21-9.

Yang, SH, Perez E, Cutright J, Liu R, He Z, Day, AL, and Simpkins JW. "Testosterone increases neurotoxicity of glutamate in vitro and ischemia-reperfusion injury in an animal model." J Appl Physiol Jan. 1, 2002 92:(1) 195-201.

* cited by examiner

USE OF 5α-ANDROSTANE (ALKYL)-3β,5,6β-TRIOL IN PREPARATION OF NEUROPROTECTIVE DRUGS

This application is a national stage filing under 35 U.S.C. §371 of International Application No. PCT/CN2011/076967 filed on Jul. 8, 2011, which claims the benefit of priority to Chinese Patent Application No. 201010224173.3 filed on Jul. 9, 2010. All of those applications are incorporated herein by reference in their entireties.

FIELD OF THE INVENTION

The present invention relates to a novel medical use of compound 5α-androstane (alkyl)-3β,5,6β-triol (hereinafter abbreviated as YC-6).

BACKGROUND OF THE INVENTION

Acute Ischemic Stroke (AIS) is conventionally treated mainly by thrombolysis or neuroprotection. Neuroprotection refers to medicament or measures, during treatment of AIS, that are able to inhibit pathological and biochemical reactions of brain tissue caused by ischemia, interfere with various pathways of ischemic cascade and prolong survival of neurons.

Neuroprotection has currently become one of the research hotspots in the field of AIS treatment. Various neuroprotectants are under clinical development, the mechanism of which is to prevent or limit brain damage resulted from ischemia by blocking various harmful pathological processes due to ischemia, so as to reduce brain tissue death and promote function recovery. The neuroprotectants can reduce cerebral infarct size; do not result in hemorrhage complication that may occur during thrombolytics or anticoagulants therapy; and can be used without confirmation of etiology, making early treatment possible. The therapeutic effect of neuroprotectants is therefore promising.

There is no neuroprotectant yet, however, that has been proven safe and effective. Drugs that are under clinical trials and have potential value of clinical application include calcium channel blockers (CCB), calcium channel modulators, glutamate release inhibitors, γ-aminobutyric acid (GABA) receptor agonists, free radical scavengers, anti-intercellular adhesion molecule antibodies, and so on.

Among various compounds, neuroactive steroids draw growing concern due to their comprehensive effect in neuroprotection. The levels of neuroactive steroids are correlated with the development and progression of some central nervous system (CNS) diseases, and play a significant role in modulating neuron damage, death, and those CNS diseases. These steroid hormones, either natural or synthetic with activity in nerve tissues, were named neuroactive steroids (NAS) since 1980s. These steroid hormones have been used clinically as replacement therapy. Estrogen is known to be one of the NAS that have the strongest neuroprotective effect. The ovaries of menopausal women do not produce estrogen again, probably leading to beta-amyloid protein (Aβ) deposition and then Alzheimer's disease (AD). Administration of estrogen can significantly reduce the levels of Aβ in brain. Clinically, estrogen treatment of AD has achieved good results. It was demonstrated that allopregnanolone protects cultured hippocampal neurons in vitro against irreversible neurotoxic insult by hypoxia or glutamate. 5α-androstane (alkyl)-3β,5,6β-triol (YC-6) is a compound, found having neuroprotective effect during our research on neurosteroids, with the following structural formula. Information retrieval until now did not reveal any reports about pharmacological effect of YC-6 or its neuroactivity/neuroprotective effect.

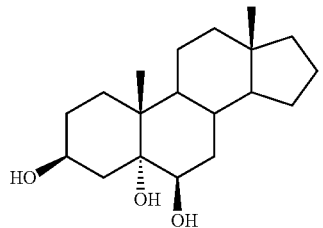 [SMILES: C[C@@]12CCCC1C1C[C@@H](O)[C@@]3(O)C[C@@H](O)CC[C@]3(C)C1CC2]

Structure of 5α-androstane(alkyl)-3β,5,6β-triol

SUMMARY OF THE INVENTION

An object of the present invention is to provide the use of 5α-androstane (alkyl)-3β,5,6β-triol in preparation of neuroprotective drugs, so as to provide a novel drug for treatment of neuron related diseases.

Our research has shown that 5α-androstane (alkyl)-3β,5,6β-triol (YC-6) significantly inhibits glutamate-induced excitotoxic damage of cerebellar granule neurons, cortical neurons, and spinal motor neurons, increases survival rate of neurons and reduces release of lactate dehydrogenase in a dose-dependent manner with minimal effective concentration of 1 μM. YC-6 also significantly inhibits damage of cerebral cortical neurons caused by ischemia in a dose-dependent manner with minimal effective concentration of 2.5 μM.

To confirm the neuroprotective effect of YC-6 in vivo, focal cerebral ischemic model and spinal cord injury model induced by abdominal aorta block were used to explore the protective effect of YC-6 against neuron damage caused by rat cerebral ischemia and rabbit spinal cord ischemia.

1 mg. $Kg^{-1}$ of YC-6 was administered via caudal vein injection to rats of YC-6 group 30 minutes prior to cerebral ischemia. The animals in YC-6 group has much higher neurological score and much smaller cerebral infarct volume than that in untreated control group, indicating that YC-6 has significant protective effect against cerebral neuron damage.

The rabbits received 2 mg. $Kg^{-1}$ of YC-6 administration 30 minutes prior to spinal cord ischemia has significant higher neurological score than that in untreated control group. No paralysis was observed in YC-6 group while all the animals in control group show paralysis. It was demonstrated histopathologically that, there remained greater amount of normal spinal cord anterior horn motor neurons in the animals of YC-6 group than that of control group, further indicating that YC-6 has significant protective effect against spinal cord neuron damage.

Taken the above evident together, YC-6 has protective effect against neuron damage caused by cerebral ischemia, spinal cord ischemia or hypoxia. No other research has reported the neuroactivity/neuroprotective effect of YC-6 so far.

survival rate of neurons, * and **: significantly different vs. Glutamate (Glu) group of cerebellar granule neurons, *P<0.05 and **P<0.01; # and ##: significantly different vs. Glutamate (Glu) group of spinal motor neurons, #P<0.05 and ##P<0.01; $ and $$: significantly different vs. Glutamate (Glu) group of cerebral cortical neurons, $P<0.05 and $$P<0.01.

Figure 2:
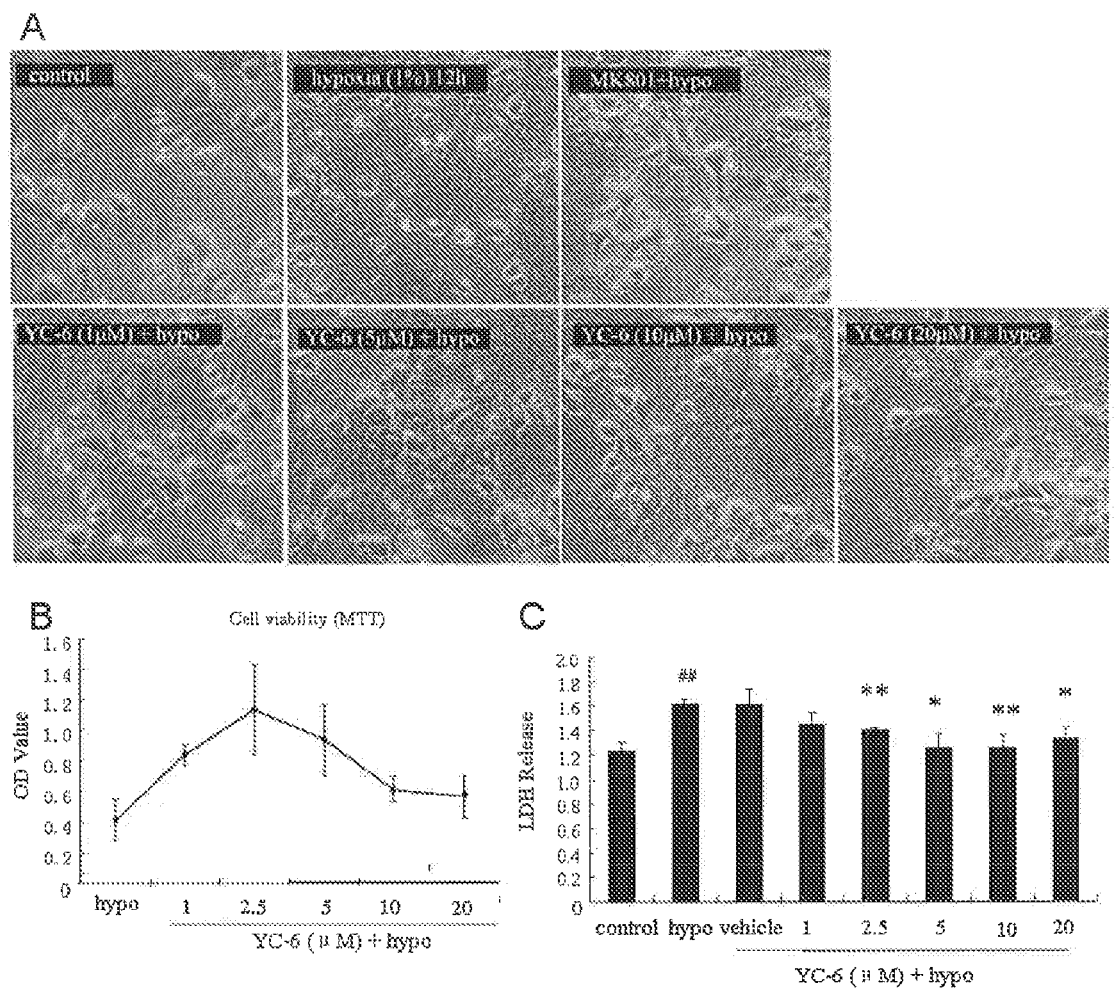

FIG. 2. The protective effect of YC-6 against hypoxia-induced cortical neuron damage. (A) the result of phase contrast microscope; (B) survival rate of neurons; (C) LDH release rate. ##: significantly different vs. control group, P<0.01; * and ** significantly different vs. hypoxia group, *P<0.05, **P<0.01.

Figure 3:
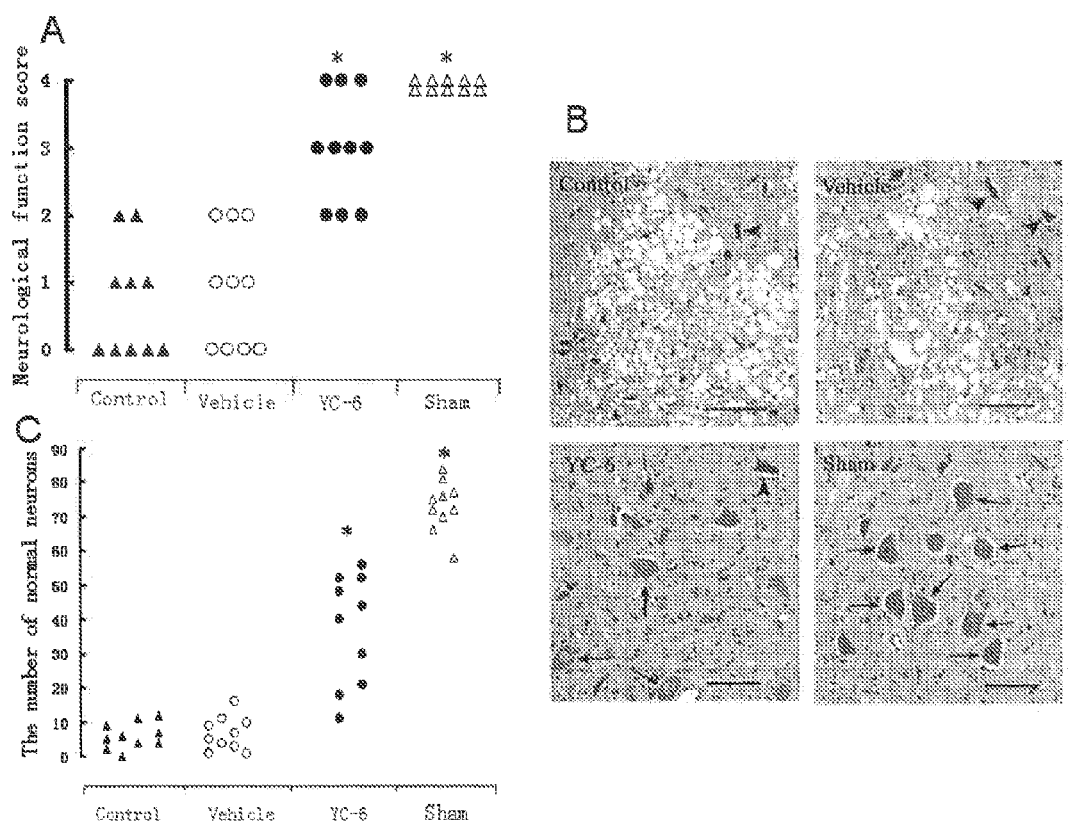

FIG. 3. The neuroprotective effect of YC-6 in rabbit spinal cord ischemia induced by abdominal aorta block. (A) neurological function score; (B) the histopathologic slices (HE staining); (C) the number of normal spinal motor neurons.

Figure 4:
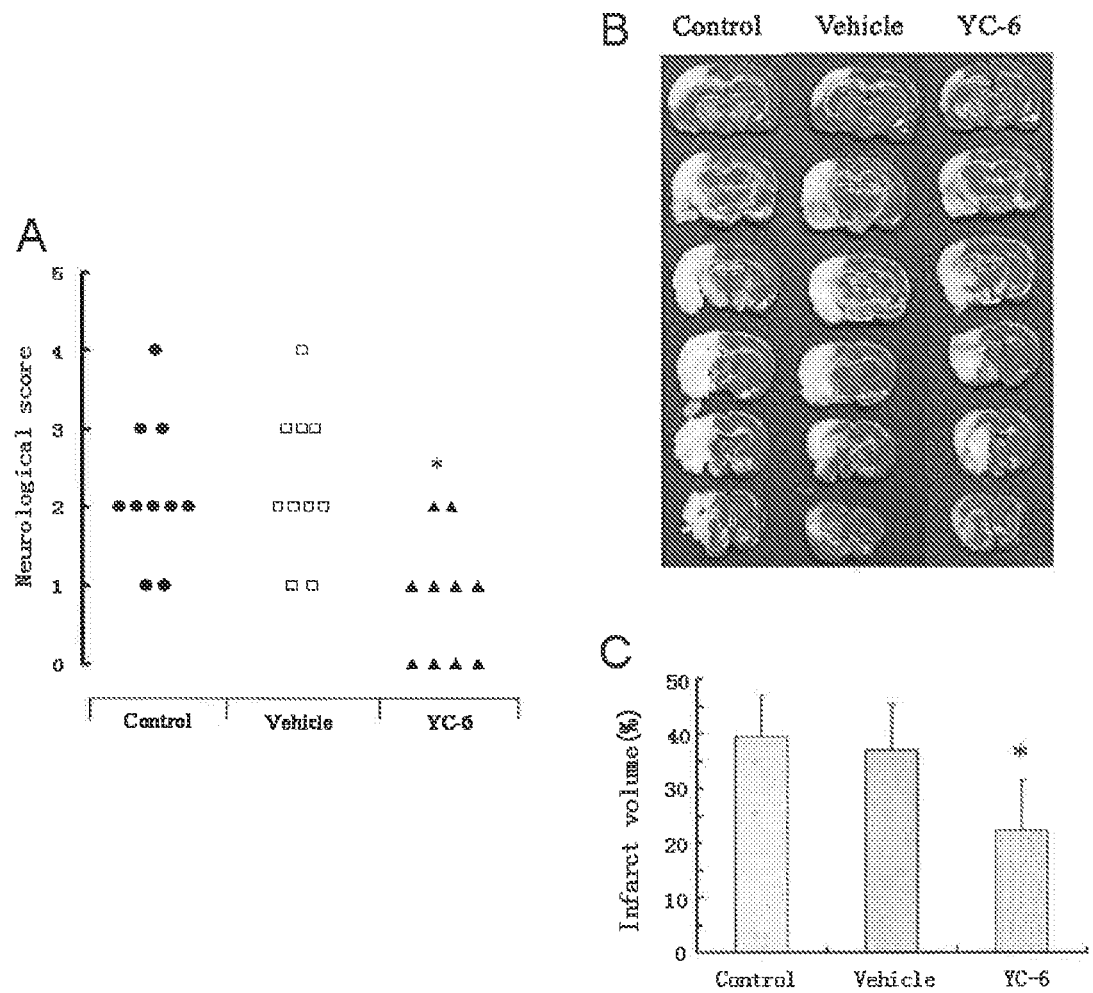

FIG. 4. The neuroprotective effect of YC-6 against rat focal cerebral ischemia. (A) neurological function score; (B) the brain slices (TTC staining); (C) comparison of cerebral infarct volume.

DETAILED DESCRIPTION OF THE INVENTION

The present invention will be described in more detail in specific examples. Yet, the present invention is not limited to the following examples.

EXAMPLE 1

Culture of Primary Neurons

1. Primary Rat Cerebellar Granule Neurons Cultures

Cerebella with meninges and blood vessels removed were obtained from 7~8 days old rats weighted 15~20 g. 0.05 g/L DNase I was used to pipette the cell to single cell suspension following 0.25 g/L trypsin digestion. The suspension was then centrifuged to collect precipitation and resuspended with BME medium containing 10% (v/v) FBS and 25 mM KCl. The cells were then seeded on dishes pre-coated with poly-lysine. 24 hours following the seeding, 10 μM Ara-C was added to inhibit growth and proliferation of non-neuron cells, such that the cerebellar granule neurons have purity not less than 95%. Glucose was added during culture to provide supplementary energy for cellular metabolism. Experiments were carried out at 8 DIV.

2. Rat Spinal Motor Neurons

Spinal cord was obtained from 15-day pregnant SD rats. The cristae membrane and blood film were removed. The spinal cord tissues of fetal rats is digested with 0.125% trypsin and then centrifuged to collect intermediate layer enriched with motor neurons. Cell debris were removed by centrifugation and cells were adhered by differential velocity adherent technique for 1 h. Suspending spinal motor neurons with slower adhering velocity were collected and seeded. 24 hours following the seeding, Ara-C was added. The Culture medium was replaced on the 3 DIV with L-15 serum free medium, followed by half medium change every 2~3 days. Experiments were carried out on the 3~5 DIV.

3. Rat Cortical Neurons

Cortex with meninges and blood vessels removed were obtained from newborn (1-day old) rats. 0.05 g/L DNase I was used to pipette the cell to single cell suspension following 0.25 g/L trypsin digestion. The suspension was then centrifuged to collect precipitation and diluted it with DMEM-F12 medium containing 5% (v/v) FBS and 2% B27. The cell was seeded on dishes pre-coated with poly-lysine. 24 hours following the seeding, 10 μM Ara-C was added to inhibit growth and proliferation of non-neuron cells. Half medium change was performed 2~3 times per week. Experiments were carried out on the 10 DIV.

EXAMPLE 2

Protective Effect of YC-6 on Primarily Cultured Neurons

1. Protective Effect of YC-6 Against Glutamate-Induced Excitotoxicity of Cerebellar Granule Neurons The cerebellar granule neurons cultured for 8 days were divided into four groups: control group, glutamate group, MK801+glutamate group, and YC-6+glutamate group. The control group received no treatment. The glutamate group was treated with 200 μM glutamate. The MK801 group and the YC-6 group were pre-treated with MK801 (10 μM) and YC-6 with different concentrations, respectively, followed by incubation at 37° C. for 30 minutes, then glutamate was added. After 24 hours, phase contrast microscope was used to observe neuronal morphologies. The cells were stained by FDA and observed under inverted fluorescent microscope for cell counting to calculate survival rate of neurons. The activity of lactate dehydrogenase(LDH) was also determined for each group.

Survival Rate=Number of live cells for each group/
Number of live cells in the control group*100%

Figure 1:
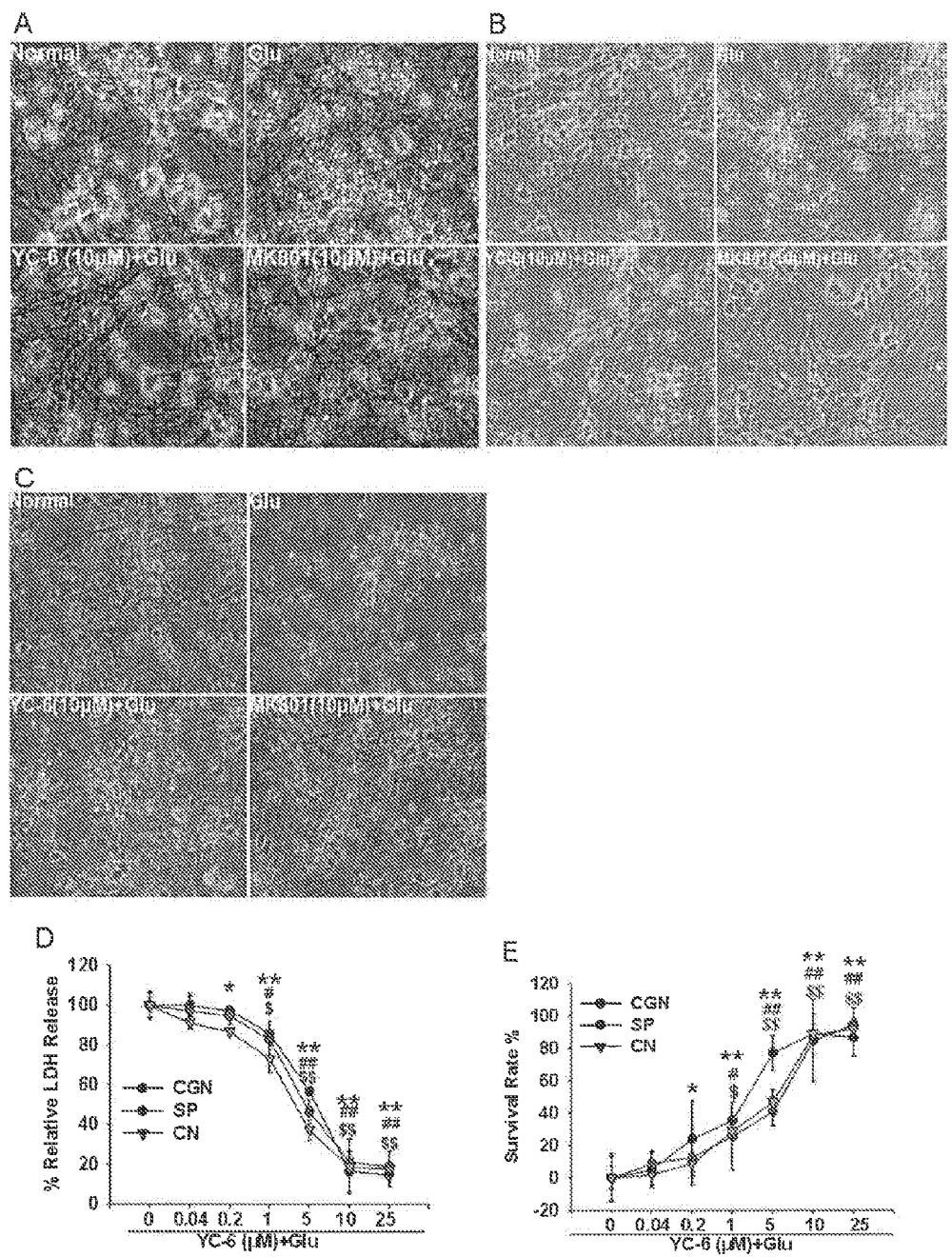
FIG. 1. The protective effect of YC-6 against glutamate-induced excitotoxicity of cerebellar granule neurons, spinal motor neurons, and cerebral cortical neurons. Morphology of (A) cerebellar granule neurons, (B) spinal motor neurons, and (C) cerebral cortical neurons; (D) LDH release rate and (E)

The results showed that the majority of cerebellar granule neurons in the YC-6+glutamate group and the MK801+glutamate group could maintain the integrity of soma and processes and had increased survival rate and decreased LDH release. Statistical differences were observed between the YC-6 and MK801 groups and the glutamate group. As shown in FIGS. 1-A, D, and E, the effect of YC-6 was concentration dependent. YC-6 showed no affect on the survival rate of normal neuron cells within the indicated dose ranges.

2. Protective Effect of YC-6 Against Glutamate-Induced Excitotoxicity of Spinal Motor Neurons The primary cultured spinal motor neurons at 5 DIV were divided into four groups: control group, glutamate group, MK801+glutamate group, and YC-6+glutamate group. The control group received no treatment. The glutamate group was treated with 200 μM glutamate. The MK801 group and the YC-6 group were pre-treated with MK801 (10 μM) and YC-6 with different concentrations, respectively, followed by incubation at 37° C. for 30 minutes, then glutamate was added. After 24 hours, phase contrast microscope was used to observe neuronal morphologies. The cells were stained by FDA and observed under inverted fluorescent microscope for cell counting to calculate survival rate of neurons. The activity of lactate dehydrogenase (LDH) was also determined for each group.

Survival Rate=Number of live cells for each group/
Number of live cells in the control group*100%

The observation of phase contrast microscope showed that a great number of living spinal motor neurons were survived in control group with intact triangle or polygon-shaped soma. The cells were stereoscopic and had halo and visible neurites. Few spinal motor neurons survived in glutamate group, although with neurites formed. Cells in this group were severely damaged. The number of spinal motor neurons in MK801+glutamate group and YC-6+glutamate group were significantly increased and many neuritis were seen although a small number of cells were dead. Compared with the control group, the survival rates of the remaining groups were decreased by different degrees. Compared with the glutamate group, the survival rate of the YC-6+glutamate group was significantly increased and YC-6 concentration dependent, as shown in FIGS. 1-B, D, and E. YC-6 showed no effect on the survival rate of normal neuron cells within the indicated dose ranges.

3. Protective Effect of YC-6 Against Glutamate-Induced Excitotoxicity of Cortical Neurons The primary cultured cortical neurons at 10 DIV were divided into four groups: control group, glutamate group, MK801+glutamate group, and YC-6+glutamate group. The control group received no treatment. The glutamate group was treated with 200 μM glutamate. The MK801 group and the YC-6 group were pre-treated with MK801 (10 μM) and YC-6 with different concentrations, respectively, followed by incubation at 37° C. for 30 minutes, then glutamate was added. After 24 hours, phase contrast microscope was used to observe neuronal morphologies. The cells were stained by FDA and observed under inverted fluorescent microscope for cell counting to calculate survival rate of neurons. The activity of lactate dehydrogenase (LDH) was also determined for each group.

Survival Rate=Number of live cells for each group/
Number of live cells in the control group*100%

The results showed that a great number of cortical neurons in the YC-6+glutamate group and the MK801+glutamate group maintained intact soma and neurites and had increased survival rates and decreased LDH release. Statistical differences were observed between the YC-6 and MK801 groups and the glutamate group. As shown in FIGS. 1-C, D, and E, the effect of YC-6 was concentration dependent. YC-6 showed no effect on the survival rate of normal neuron cells within the indicated dose ranges.

4. Protective Effect of YC-6 Against Hypoxia-Induced Damage of Cortical Neurons

The primary cultured cortical neurons at 10 DIV were divided into four groups: control group, hypoxia group, MK801 hypoxia group, and YC-6+ hypoxia group. 3 duplicates wells were provided for each group. The control group was incubated in $CO_2$ normoxic incubator. The hypoxia group was placed in a hypoxia work station (oxygen concentrate: 1%). The MK801+ hypoxia group and YC-6+ hypoxia group were pretreated with MK801 (10 μM) and YC-6 with different concentrations 30 min before replaced to hypoxia work station (oxygen concentrate: 1%). After 12 hours, the cells were observed and photographed under phase contrast microscope.

The treatment was performed in 96-well plates. 200 μl MTT stock solution was added to each well and incubated for 4 h. Hyacinthine colored crystals were formed in live cells. The liquid in each well was removed and replaced with 150 μl DMSO to dissolve the crystals. The crystals were dissolved after half an hour and OD value was detected at 570 nm wavelength by Microplates-Reader. 50 μL of culture medium was obtained from all groups at different time points and LDH release was determined for each well according to the supplier's instructions. Data were presented as the mean±SD, one-way ANOVA and statistically analyzed using paired-samples t-test and analysis of variance among means of multiple samples. See references [1] and [2]. [1] Brewer G J. Isolation and culture of aldut rat hippocampal neurons. *J. Neurosci. Meth*. 1997, 71:143-155. [2] Lee M. M., Hseih M. T. Magnolol protects cortical neuronal cells from chemical hypoxia in rats. *Neuroreport* 1998, 9:3451~3456.

The results showed primary cultured rat cortical neurons at 10 DIV were cone-shaped or multi-pole shaped with bright soma, clear boundary and nucleus. The cells had very high refractivity and neurites were connected to form a network.

Cortical neurons exposed to hypoxia were shown a disrupted integrity and decreased refractivity. Neurites were broken or disappeared. Cytoplasm was undergone granular degeneration. Some of soma was swollen or disappeared.

Compared with the control group, MK801+ hypoxia group and YC-6+ hypoxia group showed no difference in morphology of cortical neuronal cells. The neuron protection effect of YC-6 was concentration dependent (FIG. 2A). MTT method showed that hypoxia treatment significantly decreased survival rate of neurons (P<0.05), while YC-6 increased the survival rate of neurons in a concentration dependent manner (FIG. 2B). LDH release data was consistent with the results of MTT method. YC-6 pretreated group relieved neuron damaged caused by hypoxia in a concentration dependent manner (FIG. 2-C, P<0.05).

EXAMPLE 3

Neuroprotective Effect of YC-6 Against Rabbit Spinal Cord Ischemia Induced by Abdominal Aorta Block 40 male New Zealand white rabbits were grouped into 4 groups (n=10): Control group for establishing rabbit spinal cord ischemia model: YC-6 group, with 2 mg·Kg$^{-1}$ steroid YC-6 intravenously injected via rabbit ear marginal vein 30 min prior to spinal cord ischemia; Vehicle group, with equivalent capacity of hydroxypropyl cyclodextrins (1 ml·Kg$^{-1}$) injected in the same way 30 min prior to spinal cord ischemia; Sham group, with only abdominal aorta exposure but no blockage.

The establishment process of rabbit spinal cord ischemia model was performed according to references [3] and [4] and our previous report [5]. [3] Celik M. et al. Erythropoietin prevents motor neuron apoptosis and neurologic disability in experimental spinal cord ischemic injury. *Proc Natl Acad Sci USA*, 2002, 99: 2258-2263. [4] Johnson S H, Kraimer J. M., Graeber G. M. Effects of flunarizine on neurological recovery and spinal cord blood flow in experimental spinal cord ischemia in rabbits. *Stroke*, 1993, 24: 1547-1553. [5] Sang H., Cao L., Qiu P., Xiong L., Wang R., Yan G Isoflurane produces delayed preconditioning against spinal cord ischemic injury via release of free radicals in rabbits. *Anesthesiology*, 2006, 105: 953-960.

Physiological parameters were obtained for each group immediately before ischemia, 10 min after ischemia and 20 min after reperfusion. Talov scoring [5] was used to obtain functional scores for each group: 0 score, complete hind limb paralysis; 1 score, visible joint movement of hind limb; 2 score, free movement of joint of hind limb but incapable of standing up; 3 score, capable of standing up but incapable of walk; 4 score, full recovery of movement function of hind limb and capable of walk as normal.

After the neurological function scoring, the rabbits were subjected to anesthesia and spinal cord tissues at lumbar segments ($L_5$-$L_7$) were obtained. The tissues were paraffin-embedded, sliced, and then subjected to HE staining. Pathological changes were observed under an optical microscope by an observer who did not know how the rabbits were grouped and normal motor neurons of anterior horn of spinal cord were countered. The counting of normal motor neurons of anterior horn of spinal cord for each animal was presented as mean value of 3 slides.

The results showed that no statistical difference (P>0.05) in physiological parameters obtained immediately before ischemia, 10 min after ischemia and 20 min after reperfusion. The neurological function score was determined and shown in FIG. 3-A. The neurological function of hind limb of rabbits in Sham group was completely normal during the whole observation (4 score); none of the rabbits in Control and Vehicle groups can stand up; 7 of rabbits in YC-6 group can stand up (3 score or higher). The neurological function scores of YC-6 and Sham groups were significantly higher than those of Control and Vehicle groups (P<0.05).

In the Control and Vehicle groups, the spinal cord tissues at lumbar segments were severely damaged, embodied as substantive disappearance of normal motor neurons and extensive vacuolar degeneration. In the YC-6 group, however, the spinal cord damage was substantively alleviated and normal motor neurons were observed (FIG. 3-B). The number of normal motor neurons of anterior horn of spinal cord in YC-6 and Sham groups was significantly increased (FIG. 3-C).

In conclusion, YC-6 is neuroprotecctive against spinal cord ischemia.

EXAMPLE 4

Neuroprotective Effect of YC-6 Against Rat Focal Cerebral Ischemic (MCAO)

30 male SD rats were randomly divided into 3 groups (n=10): Control group, for establishment of rat focal cerebral ischemic model; YC-6 group, with 1 mg·Kg$^{-1}$ YC-6 intravenously injected via tail vein 30 min prior to cerebral ischemia; Vehicle group, with equivalent capacity of hydroxypropyl cyclodextrins (2 ml·Kg$^{-1}$) injected in the same way 30 min prior to cerebral ischemia.

The rats were subjected to postoperative fasting for 12 hours and while allowed to drink freely. Middle cerebral artery occlusion (MCAO) model was established by intraluminal thread technique [6]. [6] Wang Q., Peng Y., Chen S., Gou X., Hu B., Du J., Lu Y. Xiong L. Pretreatment with electroacupuncture induces rapid tolerance to focal cerebral ischemia through regulation of endocannabinoid system. *Stroke*, 2009, 40(6): 2157-2164. After occlusion for 120 min, the thread was released and followed by reperfusion continued. Regional cerebral blood flow was monitored by laser Doppler blood flow meter. The animals were returned to cage when waked and allowed to drink and eat freely. 72 h of reperfusion after cerebral ischemia, Longa scoring method [7] was used to assess and score neurological function by an observer who did not know how the rats were grouped: grade 0, without dysfunction; grade 1, incapable of stretching left forelimb; grade 2, rotation towards left; grade 3, falling towards left; grade 4, without autonomnic activities accompanied by conscious inhibition; grade 5, death. [7] Longa E. Z., Weinstein P. R. Carlson S., Cummins R. Reversible middle cerebral artery occlusion without craniectomy in rats. *Stroke*, 1989, 20(1): 84-91.

After neurological function scoring, the rats were sacrificed and brains were rapidly taken out. After sliced, the brain sections were immediately stained in TTC solution for 30 mins, followed by paraformaldehyde fixation. After 24 h, the slides were photographed using digital camera and images were imported into computer. Image processing software (ADOBE, PHOTOSHOP 8.0) was used to calculate infarct volume (normal brain tissue shown in pink and infarct area shown in white). In order to calibrate deviation in infarct volume caused by cerebral edema, the infarct volume was presented as percentage of normal volume in the opposite side.

Infarct volume=(Normal tissue volume of opposite side−normal tissue volume of corresponding side)/normal tissue volume of opposite side*100%

The neurological behavior scoring (NBS) was tested using Kruskal-Wallis test. If difference was present between groups, Mann-Whitney U test and Bonferroni calibration were used for paired comparison. Infarct volume and physiological parameters were presented as mean±SD error and analyzed using one-way ANOVA following Post hoc Studeng-Newman-Keuls (SNK) test for paired comparison among multiple groups. *P<0.05 indicates statistical difference.

The neurological function scores for animals in each group were shown in FIG. 4. Compared to Control and Vehicle groups, YC-6 group has significant improvement in neurological function and reduced infarct volume (*P<0.05).

Taken the above evident together, YC-6, i.e., 5α-androstane(alkyl)-3β,5,6β-triol has protective effect against neuronal injuries caused by hypoxia, cerebral ischemia or spinal cord ischemia.

What is claimed is:

1. A method for treating a neuron injury, comprising administering to a subject in need of the treatment a pharmaceutical composition comprising 5α-androstane(alkyl)-3β,5,6β-triol:

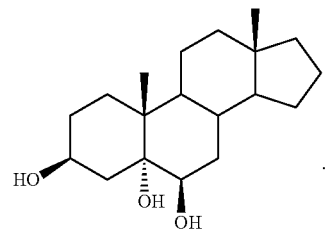

2. The method of claim 1, wherein the neuron injury occurs in cerebral ischemia.

3. The method of claim 1, wherein the neuron injury occurs in spinal cord ischemia.

4. The method of claim 1, wherein the neuron injury occurs in neuron damage caused by hypoxia.

* * * * *

UNITED STATES PATENT AND TRADEMARK OFFICE
CERTIFICATE OF CORRECTION

| | | |
|---|---|---|
| PATENT NO. | : 8,809,309 B2 | |
| APPLICATION NO. | : 13/805436 | |
| DATED | : August 19, 2014 | |
| INVENTOR(S) | : Yan et al. | |

It is certified that error appears in the above-identified patent and that said Letters Patent is hereby corrected as shown below:

On the Title Page

Item (54), in the Title, lines 1-2,
 "5α-ANDROSTANE (ALKYL)-3β,5,6β-TRIOL" should read
 --5α-ANDROSTANE-3β,5,6β-TRIOL--.

Item (87), in the PCT Publication Data, line 2,
 "PCT Pub. Date: Dec. 1, 2012" should read
 --PCT Pub. Date: Jan. 12, 2012--.

Item (30), in the "Foreign Application Priority Data",
 "Jul. 9, 2010 (CN) ........................ 2010 1 0224173" should read
 --Jul. 9, 2010 (CN) ........................ 201010224173.3--.

Item (57), in the Abstract, line 1,
 "5α-androstane(alkyl)-3β,5,6β-triol" should read
 --5α-androstane-3β,5,6β-triol--.

In the Specification

Col. 1, Lines 1-2,
 "5α-androstane (alkyl)-3β,5,6β-triol" should read
 --5α-androstane-3β,5,6β-triol--.

Col. 1, Line 15,
 "5α-androstane (alkyl)-3β,5,6β-triol" should read
 --5α-androstane-3β,5,6β-triol--.

Signed and Sealed this
Eighth Day of September, 2015

Michelle K. Lee
*Director of the United States Patent and Trademark Office*

CERTIFICATE OF CORRECTION (continued)
U.S. Pat. No. 8,809,309 B2

Col. 1, Lines 64-65,
"5α-androstane (alkyl)-3β,5,6β-triol" should read
--5α-androstane-3β,5,6β-triol--.

Col. 2, Lines 14,
"5α-androstane(alkyl)-3β,5,6β-triol" should read
--5α-androstane-3β,5,6β-triol--.

Col. 2, Lines 21,
"5α-androstane (alkyl)-3β,5,6β-triol" should read
--5α-androstane-3β,5,6β-triol--.

Col. 2, Lines 24-25,
"5α-androstane (alkyl)-3β,5,6β-triol" should read
--5α-androstane-3β,5,6β-triol--.

Col. 8, Lines 28-29,
"5α-androstane(alkyl)-3β,5,6β-triol" should read
--5α-androstane-3β,5,6β-triol--.

In the Claims

Claim 1, Col. 8, Lines 37-38,
"5α-androstane(alkyl)-3β,5,6β-triol" should read
--5α-androstane-3β,5,6β-triol--.